US008290713B2

(12) United States Patent
Kohlhoff et al.

(10) Patent No.: US 8,290,713 B2
(45) Date of Patent: Oct. 16, 2012

(54) METHOD FOR PREDICTING PROTEIN AGGREGATION AND DESIGNING AGGREGATION INHIBITORS

(75) Inventors: Kai J. Kohlhoff, Mountain View, CA (US); Jesus Zurdo, Cambridge (GB); Michele Vendruscolo, Cambridgeshire (GB)

(73) Assignee: Lonza Biologics PLLC, Slough, Berkshire (GB)

( * ) Notice: Subject to any disclaimer, the term of this patent is extended or adjusted under 35 U.S.C. 154(b) by 123 days.

(21) Appl. No.: 12/376,233

(22) PCT Filed: Jul. 24, 2007

(86) PCT No.: PCT/GB2007/002789
§ 371 (c)(1),
(2), (4) Date: Feb. 26, 2010

(87) PCT Pub. No.: WO2008/015384
PCT Pub. Date: Feb. 7, 2008

(65) Prior Publication Data
US 2010/0160602 A1 Jun. 24, 2010

Related U.S. Application Data

(60) Provisional application No. 60/821,553, filed on Aug. 4, 2006.

(51) Int. Cl.
*G01N 33/48* (2006.01)

(52) U.S. Cl. ........................................................ 702/19

(58) Field of Classification Search ........................ None
See application file for complete search history.

(56) References Cited

FOREIGN PATENT DOCUMENTS
WO       2005045442       5/2005

OTHER PUBLICATIONS

Sciarletta et al Methods in Enzymology, vol. 413, 2006, pp. 273-3127.*
Uversky, VN Natively Unfolded Proteins: A point where biology waits for physics, Protein Sci. 11:739-756 (2002).
Evans, MS et al. Conformations of co-translational folding intermediates, Prot, Pept. Let. 12(2): 189-198 (2005).
Dobson, CM, Protein Folding and Misfolding, Nature, 426:884-890 (2003).
Vendruscolo, M. et al., Protein Folding and Misfolding: A paradigm of self-assembly and regulation in complex biological systems, Phil. Trans. R. Soc. Lond. A 361:1205-1222 (2003).
Hebert, Le et al., Alzheimer Disease in the U.S. Population: Prevalence Estimates Using the 2000 Census, Arch. Neurol. 60: 1119-1122 (2003).
Evans, DA et al., Prevelance of Alzheimer's Disease in a Community Population of Older Persons. Higher than Previously Reported, JAMA 262: 2551-2556 (1989).
Lozano, AM et al., New Movements in Parkenson's, Sci. Am., 291(1): 68-75 (2005).
Berman, HM et al., The Protein Data Bank, Nuc. Acids Res. 28: 235-242 (2000).
Dubay, KF et al., Prediction of the Absolute Aggregation Rates of Amyloidogenic Polypeptide Chains, J. Mol. Biol. 341:1317-1326 (2004).
Pawar, AP et al., Prediction of "aggregation-prone" and "aggregation-susceptible" regions in proteins associated with neurodegenerative diseases, J. Mol. Biol. 350: 379-392 (2005).
Junn, E. et al., Human α-synuclein over-expression increases interacellular reactive oxygen specied levels and susceptibility to dopamine, Neurosci Lett. 320: 146-50 (2002).
Lev, N. et al., Proteasonmal inhibition hypersensitizes differentiated neuroblastoma cells to oxidative damage, Neurosci Lett. 399:27-32 (2006).
McGowan, E. et al., A decade of modeling Alzheimer's disease in transgenic mice, Trends Genet. 22: 281-9 (2006).
Whitworth, AJ et al., *Drosophila* models pioneer a new approach to drug discovery for Parkinson's disease, Drug Discov Today. 11(3-4): 119-26 (Feb. 2006).
Heon, E. et al., The γ-Crystallins and Human Cataracts: A Puzzle Made Clearar, Am. J. Hum. Genet. 65:1261-1267 (1999).
Dahm, R., Dying to see, Sci, Am., 291(4): 82-89 (2004).
Pande, A. et al., Crystal cataracts: Human genetic cataract caused by protein crystallization, PNAS, 98(11): 6116-6120 (2001).
Spillantini, MG et al., α-Synuclein in Lewy bodies, Nature. 388: 839-840 (1997).
Selkoe, DJ, Alzheimer's disease is a synaptic failure, Science 298: 789-791(2002).
Das, B. et al., Performance of hybrid methods for large-scale unconstrained optimization as applied to models of proteins, J Comput. Chem. 24:1222-31 (2003).
de Bakker, PL, et al., Ab initio construction of polypeptide fragments: Accuracy of loop decoy discrimination by an all-atom statistical potential and the AMBER force field with the Generalized Born salvation model, Proteins, 51(1): 21-40 (2003).
de Groot, NS, et al., Prediction of hot spots of aggregation in disease-linked polypeptides, BMC Structural Biology, vol. 5 No. 18 (Sep. 2005), pp. 1-15.
Aravinda, S. et al., Structure and Assemply of Designed beta-Hairpin Peptides in Crystals as Models for beta-Sheet Aggregation, Biochemistry, vol. 43, No. 7, 1832-1846 (Feb. 2004).
International Search Report issued in International Application No. PCT/GB2007/002789 dated Nov. 11, 2007 (6 pages).
Written Opinion issued in International Application No. PCT/GB2007/002789 dated Nov. 11, 2007 (7 pages).
Office Action issue in corresonding Chinese Application No. 200780029032.2 dated Aug. 23, 2010. (13 pages).
Office Action issued in corresponding Eurasian Application No. 200970180 dated Nov. 29, 2010 (3 pages).
Notice of Allowance issued in corresponding Chinese Application No. 200780029032.2 dated Jul. 29, 2011 (18 pages).
Notice of Acceptance issued in Australian Patent Application No. 2007280282 dated Jan. 13, 2012, 3 pages.

* cited by examiner

*Primary Examiner* — Michael Borin
(74) *Attorney, Agent, or Firm* — Osha • Liang LLP

(57) ABSTRACT

The present invention provides methods of predicting protein aggregation and designing aggregation inhibitors. One such method for predicting potential protein aggregation inhibiting peptide sequences, includes the steps of: a) identifying a peptide sequence forming at least part of an aggregation region in a target protein; b) testing whether said peptide sequence forms part of a β-sheet; c) if a positive result is achieved in step b), extracting the adjacent strands of that sheet; d) identifying residues in the adjacent strands to said peptide sequence whose side chains interact with said peptide sequence, those residues forming a potential protein aggregation inhibiting peptide sequence. The present invention also provides methods of designing compounds using the residues identified in the above method; compounds produced by the methods and computer programs for carrying out the above methods.

27 Claims, 12 Drawing Sheets

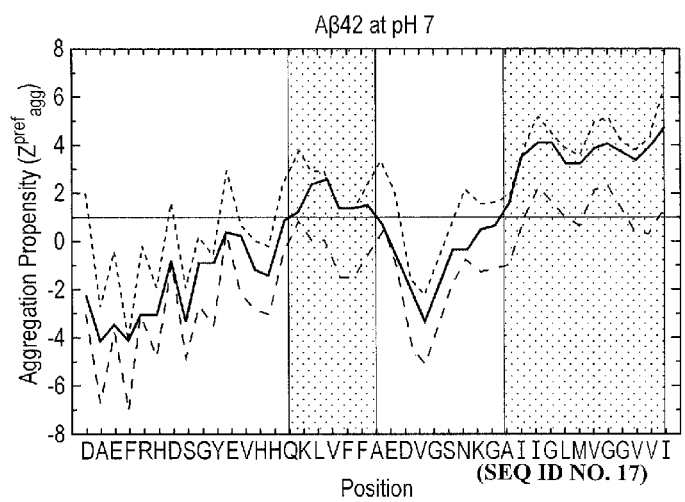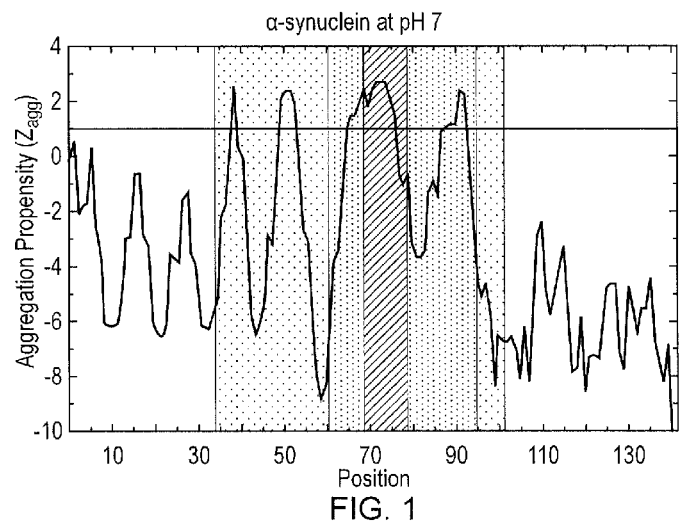
FIG. 1

```
Hit 1 at entry 56227
******************************************************************
1u8s_A mol:protein length:192    Glycine Cleavage System Transcriptional Repr
SARUDSGC
SARUDSGC Query pattern >SARUDSGC< found at position: 146 (SEQ ID NO. 18)
Structure:      >EEEE TTS<
sequence  neighbourhood:  ...FHIAISARUDSGCNLMQL... (SEQ ID NO. 19)
Structure neighbourhood:  ...EEEEEEEE TTS HHHH...
Total length of sequence : 192
Total length of structure: 192
Opening existing file pdb1U8S.ent
# residues in PDB record : 171

4 residues of query sequence overlap with following beta-sheet:
Hit: startPos = 146, endPos = 153; sheet: first = 140, last = 149
SHEET     2   B 4 GLN A 140  VAL A 149 -1  O  SER A 146   N  ALA A 122

MASLSAQTI (SEQ ID NO. 20)
URASIAIHFQ (SEQ ID NO. 21)
YTUEUYUES (SEQ ID NO. 22)
Hydrogen bonds prediction completed
******************************************************************
```

FIG. 3a

```
First ten lines from pdb_seqres.txt

>1pr2_A mol:protein length:239    Purine Nucleoside Phosphorylase
MATPHINAEMGDFADVVLMPGDPLRAKYIAETFLEDAREVNNVRGMLGFTGTYKGRKISVMGHGMGIPSCSIYTK
ELITDFGVKKIIRVGSCGAVLPHVKLRDVVIGMGACTDSKVNRIRFKDHDFAAIADFDMVRNAVDAAKALGIDAR
VGNLFSADLFYSPDGEMFDVMEKYGILGVEMEAAGIYGVAAEFGAKALTICTVSDHIRTHEQTTAAERQTTFNDM
IKIALESVLLGDKE (SEQ ID NO. 23)
>1pr2_B mol:protein length:239    Purine Nucleoside Phosphorylase
MATPHINAEMGDFADVVLMPGDPLRAKYIAETFLEDAREVNNVRGMLGFTGTYKGRKISVMGHGMGIPSCSIYTK
ELITDFGVKKIIRVGSCGAVLPHVKLRDVVIGMGACTDSKVNRIRFKDHDFAAIADFDMVRNAVDAAKALGIDAR
VGNLFSADLFYSPDGEMFDVMEKYGILGVEMEAAGIYGVAAEFGAKALTTCTVSDHIRTHEQTTAAERQTTFNDM
IKIALESVLLGDKE (SEQ ID NO. 23)
```

FIG. 5

```
First ten lines from ss.txt:

>1PR2:A
  BTTB   TTSS SEEEESSTHHHHHHHT BS EE B GGG EEEEEETTEEEEE   SSHHHHHHHHH
HHHHHS  EEEEEEEEE STTTTTT EEEESEEES SHHHHTTTS   B  HHHHHHHHHHHHT   EE
EEEEEE S SS S TTHHHHHHHT EEESSHHHHHHHHHHTT EEEEEEE EETTS  HHHHHHHHHHH
HHHHHHHHHHHH
>1PR2:B
   SS   TTSS SEEEE SSHHHHHHHHHH BS EE B GGG EEEEEETTEEEEE   SSHHHHHHHHH
HHHHHS  EEEEEEEEE STTTTTT EEEESEEES SHHHHTTTS   B  HHHHHHHHHHHHT    E
EEEEEE S SS SSTTHHHHHHHT EEESSHHHHHHHHHHTT EEEEEEE EETTT  HHHHHHHHHHH
HHHHHHHHHHHH
```

FIG. 5A

| | |
|---|---|
| OUTPUTTO 2005_08_19_14h11m01s/images/hit38.png<br>NUMATOMS 9<br>NUMBONDS 4<br>RESID THR 188<br>RESID VAL 189<br>RESID SER 190<br>RESID ILE 60<br>RESID ASN 61<br>BOND ASN 61SER 188<br>RESID PHE 62<br>RESID SER 63<br>BOND SER 63THR 190<br>RESID GLY 148<br>BOND GLY 148PHE 61<br>RESID SER 149<br>BOND SER 149ASN 62 | Predicted hydrogen bonds<br><br>T V S<br><br>I N F S  (SEQ ID NO. 24)<br><br>G S |

FIG. 7

SEQUENCE LISTING

<160> NUMBER OF SEQ ID NOS: 30

<210> SEQ ID NO 1
<211> LENGTH: 24
<212> TYPE: PRT

-continued

<213> ORGANISM: Homo sapiens

<400> SEQUENCE: 1

Ser Ala Arg Val Asp Ser Gly Cys Trp Met Leu Tyr Glu Gln Pro Asn
1               5                   10                  15

Tyr Ser Gly Leu Gln Tyr Phe Leu
            20

<210> SEQ ID NO 2
<211> LENGTH: 24
<212> TYPE: PRT
<213> ORGANISM: Artificial sequence
<220> FEATURE:
<223> OTHER INFORMATION: Synthetic sequence: Inverted mutCRYD34-58
      sequence

<400> SEQUENCE: 2

Leu Phe Tyr Gln Leu Gly Ser Tyr Asn Pro Gln Glu Tyr Leu Met Trp
1               5                   10                  15

Cys Gly Ser Asp Val Arg Ala Ser
            20

<210> SEQ ID NO 3
<211> LENGTH: 4
<212> TYPE: PRT
<213> ORGANISM: Artificial sequence
<220> FEATURE:
<223> OTHER INFORMATION: Synthetic sequence: Search string

<400> SEQUENCE: 3

Gln Ala Asn Thr
1

<210> SEQ ID NO 4
<211> LENGTH: 4
<212> TYPE: PRT
<213> ORGANISM: Artificial sequence
<220> FEATURE:
<223> OTHER INFORMATION: Synthetic sequence: Search string

<400> SEQUENCE: 4

Asn Ala Asn Thr
1

<210> SEQ ID NO 5
<211> LENGTH: 4
<212> TYPE: PRT
<213> ORGANISM: Artificial sequence
<220> FEATURE:
<223> OTHER INFORMATION: Synthetic sequence: Search string

<400> SEQUENCE: 5

Gln Ala Gln Thr
1

<210> SEQ ID NO 6
<211> LENGTH: 4
<212> TYPE: PRT
<213> ORGANISM: Artificial sequence
<220> FEATURE:
<223> OTHER INFORMATION: Synthetic sequence: Search string

<400> SEQUENCE: 6

Asn Ala Gln Thr
1

```
<210> SEQ ID NO 7
<211> LENGTH: 14
<212> TYPE: PRT
<213> ORGANISM: Artificial sequence
<220> FEATURE:
<223> OTHER INFORMATION: Synthetic sequence

<400> SEQUENCE: 7

Ala Asp Asp Tyr Tyr Thr Ala Thr Gly His Trp Tyr Ala Thr
1               5                   10

<210> SEQ ID NO 8
<211> LENGTH: 4
<212> TYPE: PRT
<213> ORGANISM: Artificial sequence
<220> FEATURE:
<223> OTHER INFORMATION: Synthetic sequence

<400> SEQUENCE: 8

Ala Asp Asp Tyr
1

<210> SEQ ID NO 9
<211> LENGTH: 5
<212> TYPE: PRT
<213> ORGANISM: Artificial sequence
<220> FEATURE:
<223> OTHER INFORMATION: Synthetic sequence

<400> SEQUENCE: 9

Thr Ala Thr Gly His
1               5

<210> SEQ ID NO 10
<211> LENGTH: 5
<212> TYPE: PRT
<213> ORGANISM: Artificial sequence
<220> FEATURE:
<223> OTHER INFORMATION: Synthetic sequence

<400> SEQUENCE: 10

Ala Thr Gly His Trp
1               5

<210> SEQ ID NO 11
<211> LENGTH: 4
<212> TYPE: PRT
<213> ORGANISM: Artificial sequence
<220> FEATURE:
<223> OTHER INFORMATION: Synthetic sequence

<400> SEQUENCE: 11

His Gly Thr Ala
1

<210> SEQ ID NO 12
<211> LENGTH: 4
<212> TYPE: PRT
<213> ORGANISM: Unknown
<220> FEATURE:
<223> OTHER INFORMATION: Putative Glycine Cleavage System
      Transcriptional Repressor (1U8S)

<400> SEQUENCE: 12

Ser Ala Arg Val
1

<210> SEQ ID NO 13
```

```
<211> LENGTH: 5
<212> TYPE: PRT
<213> ORGANISM: Homo sapiens

<400> SEQUENCE: 13

Ser Ala Arg Val Asp
1               5

<210> SEQ ID NO 14
<211> LENGTH: 5
<212> TYPE: PRT
<213> ORGANISM: Homo sapiens

<400> SEQUENCE: 14

Pro Asn Tyr Ser Gly
1               5

<210> SEQ ID NO 15
<211> LENGTH: 5
<212> TYPE: PRT
<213> ORGANISM: Homo sapiens

<400> SEQUENCE: 15

Glu Gln Val Thr Asn
1               5

<210> SEQ ID NO 16
<211> LENGTH: 5
<212> TYPE: PRT
<213> ORGANISM: Homo sapiens

<400> SEQUENCE: 16

Val Thr Gly Val Thr
1               5

<210> SEQ ID NO 17
<211> LENGTH: 41
<212> TYPE: PRT
<213> ORGANISM: Homo sapiens

<400> SEQUENCE: 17

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile
        35                  40

<210> SEQ ID NO 18
<211> LENGTH: 8
<212> TYPE: PRT
<213> ORGANISM: Homo sapiens

<400> SEQUENCE: 18

Ser Ala Arg Val Asp Ser Gly Cys
1               5

<210> SEQ ID NO 19
<211> LENGTH: 18
<212> TYPE: PRT
<213> ORGANISM: Unknown
<220> FEATURE:
<223> OTHER INFORMATION: Putative Glycine Cleavage System
      Transcriptional Repressor (1U8S)

<400> SEQUENCE: 19
```

```
Phe His Ile Ala Ile Ser Ala Arg Val Asp Ser Gly Cys Asn Leu Met
1               5                   10                  15

Gln Leu

<210> SEQ ID NO 20
<211> LENGTH: 9
<212> TYPE: PRT
<213> ORGANISM: Unknown
<220> FEATURE:
<223> OTHER INFORMATION: Putative Glycine Cleavage System
      Transcriptional Repressor (1U8S)

<400> SEQUENCE: 20

Met Ala Ser Leu Ser Ala Gln Thr Ile
1               5

<210> SEQ ID NO 21
<211> LENGTH: 10
<212> TYPE: PRT
<213> ORGANISM: Unknown
<220> FEATURE:
<223> OTHER INFORMATION: Putative Glycine Cleavage System
      Transcriptional Repressor (1U8S)

<400> SEQUENCE: 21

Gln Phe His Ile Ala Ile Ser Ala Arg Val
1               5                   10

<210> SEQ ID NO 22
<211> LENGTH: 9
<212> TYPE: PRT
<213> ORGANISM: Unknown
<220> FEATURE:
<223> OTHER INFORMATION: Putative Glycine Cleavage System
      Transcriptional Repressor (1U8S)

<400> SEQUENCE: 22

Tyr Thr Val Glu Val Tyr Val Glu Ser
1               5

<210> SEQ ID NO 23
<211> LENGTH: 239
<212> TYPE: PRT
<213> ORGANISM: Unknown
<220> FEATURE:
<223> OTHER INFORMATION: Purine Nucleoside Phosphorylase (1pr2)

<400> SEQUENCE: 23

Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Met Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
```

```
                115                 120                 125
Ile Ala Asp Phe Asp Met Val Arg Asn Ala Val Asp Ala Ala Lys Ala
            130                 135                 140

Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
                195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Glu
225                 230                 235

<210> SEQ ID NO 24
<211> LENGTH: 4
<212> TYPE: PRT
<213> ORGANISM: Unknown
<220> FEATURE:
<223> OTHER INFORMATION: Endo-1,4-Beta Xylanase II

<400> SEQUENCE: 24

Ile Asn Phe Ser
1

<210> SEQ ID NO 25
<211> LENGTH: 5
<212> TYPE: PRT
<213> ORGANISM: Unknown
<220> FEATURE:
<223> OTHER INFORMATION: Endo-1,4-Beta Xylanase II

<400> SEQUENCE: 25

Gly Ser Tyr Asn Pro
1               5

<210> SEQ ID NO 26
<211> LENGTH: 15
<212> TYPE: PRT
<213> ORGANISM: Unknown
<220> FEATURE:
<223> OTHER INFORMATION: Endo-1,4-Beta Xylanase II

<400> SEQUENCE: 26

Val Ile Asn Phe Ser Gly Ser Tyr Asn Pro Asn Gly Asn Ser Tyr
1               5                   10                  15

<210> SEQ ID NO 27
<211> LENGTH: 9
<212> TYPE: PRT
<213> ORGANISM: Unknown
<220> FEATURE:
<223> OTHER INFORMATION: Endo-1,4-Beta Xylanase II

<400> SEQUENCE: 27

Ser Gly Ser Ala Ser Ile Thr Val Ser
1               5

<210> SEQ ID NO 28
<211> LENGTH: 11
<212> TYPE: PRT
<213> ORGANISM: Unknown
```

```
-continued

<220> FEATURE:
<223> OTHER INFORMATION: Endo-1,4-Beta Xylanase II

<400> SEQUENCE: 28

Val Ile Asn Phe Ser Gly Ser Tyr Asn Pro Asn
1               5                   10

<210> SEQ ID NO 29
<211> LENGTH: 4
<212> TYPE: PRT
<213> ORGANISM: Unknown
<220> FEATURE:
<223> OTHER INFORMATION: Endo-1,4-Beta Xylanase II

<400> SEQUENCE: 29

Gly Ser Val Asn
1

<210> SEQ ID NO 30
<211> LENGTH: 42
<212> TYPE: PRT
<213> ORGANISM: Homo sapiens

<400> SEQUENCE: 30

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

METHOD FOR PREDICTING PROTEIN AGGREGATION AND DESIGNING AGGREGATION INHIBITORS

The present invention relates to methods of predicting protein aggregation and designing aggregation inhibitors. It is particularly, but not exclusively, concerned with methods which assist in the design of compounds for stabilisation of proteins against aggregation, thus potentially increasing the shelf-life of proteins, decreasing immunogenicity of proteins and increasing yields in in vitro translation systems.

BACKGROUND TO THE INVENTION

Deposits of misfolded proteins in cells or in intracellular space are found to play a role in a number of severe medical disorders, among which are diseases such as Alzheimer's, Parkinson's, and type-2 diabetes. The costs incurred by the health care systems worldwide for treating those medical conditions are massive, as is the impact onto the lives of those that are affected and their families.

The number of cases is likely to increase steadily as life expectancy rises. To address this growing problem, new therapies are being developed based on interfering at early stages with the ability of proteins to form aggregates.

The typical life cycle of a protein in the cell begins with synthesis of the polypeptide at the ribosome and continues from an initially unfolded state via a folding pathway, which might involve one or several folding intermediates, to the biologically-active native state of the protein. For most proteins, this native state corresponds to a closely folded conformation, although some exceptions exist, one of which is α-synuclein, which is natively unfolded (Uversky V N (2002) *Natively unfolded proteins: A point where biology waits for physics*, Protein Sci. 11:739-756). The life cycle ends with denaturation and degradation.

The cell possesses sophisticated quality control mechanisms that assist the folding process of the protein. The first of these is the ribosome itself. In the second, the protein is supported by heat shock proteins and chaperones that act as catalyst or promoter to fold a protein in the correct way, or to refold misfolded proteins (Evans M S, Clarke T F IV, Clark P L (2005) *Conformations of Co-Translational Folding Intermediates*, Prot, Pept. Let. 12(2): 189-195).

In the case that refolding fails, misfolded proteins are processed by the ubiquitin-proteasome system. In a first step, ubiquitin is being attached to faulty structures. These tags mark the polypeptide chain for degradation and this task is fulfilled by the proteasome. A more detailed description of folding and misfolding processes can be found in Dobson C M (2003) *Protein folding and misfolding*, Nature 426: 884-890 and Vendruscolo M, Zurdo J, MacPhee C E, Dobson C M (2003) *Protein folding and misfolding: a paradigm of self-assembly and regulation in complex biological systems*, Phil. Trans. R. Soc. Lond. A 361: 1205-1222).

However, the quality control of the cell can fail for a variety of reasons, leading to accumulation of misfolded proteins. These proteins can then aggregate forming dense structures called amyloid fibrils with a core region consisting of continuous assemblies of β-sheets (Dobson C M (2005) *Prying into prions*, Nature 435: 747-749).

In living tissue, protein deposition (often in the form of amyloid aggregates) is frequently associated with a variety of diseases, many of which are age related. For example, these diseases include neurodegenerative diseases such as Parkinson's, Alzheimer's and spongiform encephalopathies, as well as systemic (such as immunoglobulin light chain or transthyretin amyloidoses) and peripheral tissue disorders (such as type-2 diabetes). In humans, more than 30 different disorders are known to be associated with protein deposition.

Particularly in the developed world, where the life expectancy continues to rise steadily, the ever-growing number of people affected with those diseases poses unprecedented and increasingly severe problems to society.

It is estimated that in the United States alone about 4.5 million people were affected by Alzheimer's disease in 2000, and the number of cases might rise to 16 million by 2050 (Hebert L E, Scherr P A, Bienias J L, Bennett D A, Evans D A (2003) *Alzheimer Disease in the U.S. Population: Prevalence Estimates Using the 2000 Census*, Arch. Neurol. 60: 1119-1122). The risk of people being affected with this neurodegenerative disease is estimated to be as high as 1 in 10 for people over 60 years of age and almost 1 in 2 for those over 85 (Evans D A, Funkenstein H H, Albert M S, Scherr P A, Cook N R, Chown M J, Hebert L E, Hennekens C H, Taylor J O (1989) *Prevalence of Alzheimer's Disease in a Community Population of Older Persons. Higher than Previously Reported*, Jama 262: 2551-2556). The impact onto the health systems is immense, and some authors predict that neurodegenerative diseases could become the leading cause of death (Lozano A M, Kalia S K (2005) *New Movements in Parkinson's*, Sci. Am., 291(1): 58-65).

Furthermore, the propensity of biomolecules to form aggregates in solution has always been one of the major problems in drug design. Therapeutic molecules must be both soluble as well as reactive and should not form aggregates when administered in relatively high concentrations or stored over long periods of time. In many cases, finding conditions in which such polypeptides are sufficiently stable proves to be time consuming and costly, and sometimes even impossible with currently available methods. Finding ways to interfere with the folding process in order to impede the formation of aggregates can therefore improve the efficiency of drug development.

SUMMARY OF THE INVENTION

Therefore, to preferably assist in the addressing of the above issues, it is desirable to be able to design compounds that interact with a pathological protein, or with a therapeutic molecule in solution, so that the compound competitively binds to and blocks the most important sites driving the aggregation process. One of the approximations to achieve this goal would involve the design of peptide-derived molecules that would interfere with the aggregation process.

Accordingly, at its broadest, an aspect of the present invention provides a method of designing protein aggregation inhibiting peptides which involves identifying peptide sequences whose side chains would interact with an aggregation-prone region in a target protein.

A first aspect of the present invention provides a method for predicting potential protein aggregation inhibiting peptide sequences, including the steps of:
a) identifying a peptide sequence forming at least part of an aggregation region in a target protein;
b) testing whether said peptide sequence forms part of a β-sheet;
c) if a positive result is achieved in step b), extracting the adjacent strands of that sheet;
d) identifying residues in the adjacent strands to said peptide sequence whose side chains interact with said peptide sequence, those residues forming a potential protein aggregation inhibiting peptide sequence.

Preferably the step of testing is carried out on a plurality of heterologous proteins to the target protein. Accordingly, even where the aggregation region in the target protein does not form part of a β-sheet, appropriate peptide sequences can be identified from similar or identical sequences found in other proteins which do form part of a β-sheet.

This testing can be performed by using a database of protein structures, and preferably tests whether said peptide sequence forms part of a β-sheet in any of the known protein structures present in that database. In embodiments of the invention, data from the Protein Data Bank (PDB) of the Research Collaboratory for Structural Bioinformatics (RCSB) is used, which contains a large number of experimental structures and theoretical models (Berman H M, Westbrook J, Feng Z, Gilliland G, Bhat T N, Weissig H, Shindyalov I N, Bourne P E (2000) *The Protein Data Bank*, Nuc. Acids Res. 28: 235-242). As of 27 Jun. 2005, there were 31639 structures in the PDB. However, other structural databases or databanks may be used.

The first step in predicting an aggregation inhibiting peptide is to identify one or more aggregation regions in the target protein, and the peptide sequences forming at least part of this region.

A preferred method of identifying this region is to use an amyloid aggregation profile. This theoretical method for the prediction of aggregation hotspots within polypeptide chains is described in DuBay K F, Pawar A P, Chiti F, Zurdo J, Dobson C M, Vendruscolo M (2004) *Prediction of the Absolute Aggregation Rates of Amyloidogenic Polypeptide Chains*, J. Mol. Biol. 341: 1317-1326 and in Pawar A P, DuBay K F, Zurdo J, Chiti F, Vendruscolo M, Dobson C M (2005) *Prediction of "aggregation-prone" and "aggregation-susceptible" regions in proteins associated with neurodegenerative diseases*, J. Mol. Biol. 350: 379-392. The method provides an algorithm that, based on a number of intrinsic properties of amino acids, can be used to calculate an amyloid aggregation propensity profile for any protein.

Once an amyloid aggregation profile has been obtained for the target protein, aggregation regions can be identified by considering the parts of the protein for which the aggregation propensity in the profile exceeds a predetermined amount (such as 1).

Alternatively or additionally, the aggregation regions can be identified by experimental measurements, for example by systematic mutation of each of the residues in a peptide or protein or fragment thereof, and synthesising fragments of such peptides or proteins or fragments and analysing their aggregation propensity in in vitro assays.

Preferably the step of testing includes the sub-steps of: identifying a group of proteins contained in a database of protein structures which contain related peptide sequences related to the peptide sequence forming at least part of an aggregation region in a target protein; and identifying within that group those proteins in which said related peptide sequences form part of a β-sheet.

In order to increase the probable number of hits (i.e. identified proteins in which the related peptide sequences form part of a β-sheet), the related peptide sequences preferably include the peptide sequence of interest and fragments of said peptide sequence.

Alternatively or additionally, to increase the probable number of hits, the related peptide sequences may include sequences which include conservative substitutions of one or more amino acids with the peptide sequence of interest.

In the context of this step, a conservative substitution is a substitution which preserves the aggregation properties of the amino acid being substituted. In particular, the conservative substitutes may be chosen on the basis of amino acids with aggregation propensities at pH 7.0 which are within 0.2 of each other. Alternatively or additionally, the conservative substitutes may be chosen on the basis of residues with similar properties (e.g. basic, acidic, hydrophobic, polar, aromatic).

More preferably the related peptide sequences include one or more of the above peptide sequences in both forward and reverse order.

In one embodiment of the present aspect, the sub-step of identifying a group of proteins contained in the database includes comparing the related peptide sequences with the residues contained in "SHEET" lines in a PDB file for the protein in question.

Alternatively or additionally, the sub-step of identifying a group of proteins contained in the database includes identifying those residues in the related peptide sequences that form hydrogen bonds with each other.

One method by which residues that form hydrogen bonds with each other may be identified is to calculate the Euclidean distance between each pair of residues which are at least three residues apart, with a hydrogen bond being assumed to form if that distance is less than 3.2 Angstrom, and more preferably if that distance is less than 3.075 Angstrom. In one embodiment, these Euclidean distances are calculated using "ATOM" entries from the PDB file for the protein in question.

Preferably the method includes the further step of displaying the identified residue pairs that form hydrogen bonds with each other, and the hydrogen bonds formed.

In order to check the validity of the results from either of the above ways of identifying the group of proteins, the results from both methods may be used to cross-check the residues identified from the other method. Such cross-checks can alternatively or additionally be performed with other methods of identifying the group of proteins.

The method preferably includes the further step of displaying the residues identified in step d), and may also include the step of displaying information about the protein from which these residues are identified. This displaying may take the form of a 3-dimensional arrangement of the identified residues in the β-sheet.

Preferably, the method includes the further step of modifying the backbone of adjacent strands and sidechains to the potential protein aggregation inhibiting peptide sequence not directly participating in the interaction with said peptide sequence forming part of an aggregation region in the target protein, to maximise interaction with said peptide sequence and increase the potential aggregation inhibition properties of the potential aggregation inhibiting sequence.

Once one or more peptide sequences or "templates" have been identified, a peptide library can be designed and synthesised which introduces variability on the regions of the template not directly involved in the interaction with the aggregation region in question. This library could then be screened using proprietary biochemical aggregation and cytotoxicity assays to investigate changes in aggregation rates and toxicity of proteins in the presence of various compounds.

The library is preferably created by adding modifications to the candidate amino acid sequence(s) that improve properties such as stability and solubility.

A method as described herein may, for example comprise: e) synthesising a peptide library, the members of said peptide library comprising the residues identified in step d), and f) determining the binding affinity of the members of said library for the target protein.

One or more peptides may be identified within the library which binds to the target protein with high affinity relative to controls. Such peptides may be candidate protein aggregation inhibiting peptides.

A peptide found to bind to the target with high affinity may be isolated, purified and/or synthesised.

Peptide sequences which have been predicted or identified as described above may be screened for interference with cellular processes (i.e. toxicology). For example, a method may comprise: testing whether the residues identified in step d) above interact with one or more non-target proteins existing in the Protein Data Bank (or any other protein database), preferably non-target proteins which could mediate essential cellular processes, such as metabolic pathways, ionic homeostasis structural proteins, proteins involved in response to stress, regulating gene expression, DNA repair, etc.

The step of testing may be carried out on a plurality of heterologous proteins to said target protein, preferably using a database of protein structures. Testing may, for example, be performed by identifying a group of proteins within the database which contain related peptide sequences which are related to the test peptide sequence; and identifying within the group those proteins in which the related peptide sequences interact with the residues identified in step d) above.

Candidate protein aggregation inhibiting peptide sequences may be identified which do not interact with proteins which mediate essential cellular processes.

The efficacy of a peptide sequence identified as described above may be determined in a model of a protein misfolding disease.

Models of protein misfolding diseases are well known in the art. Suitable models include cells which over-express an aggregation-prone protein, and transgenic animal models such as mouse or *drosophila* models which over-express an aggregation-prone and that might or not be exposed to other challenges, such as oxidative stress, etc.

For example, see:

Junn E, Mouradian M M, *Human alpha-synuclein over-expression increases intracellular reactive oxygen species levels and susceptibility to dopamine*, Neurosci Lett. 2002; 320:146-50.

Lev N, Melamed E, Offen D, *Proteasomal inhibition hypersensitizes differentiated neuroblastoma cells to oxidative damage*, Neurosci Lett. 2006; 399:27-32.

McGowan E, Eriksen J, Hutton M, *A decade of modeling Alzheimer's disease in transgenic mice*, Trends Genet. 2006; 22:281-9.

Whitworth A J, Wes P D, Pallanck L J, *Drosophila models pioneer a new approach to drug discovery for Parkinson's disease*, Drug Discov Today. 2006 February; 11(3-4):119-26.

Aggregation-prone proteins include the following proteins, precursors or fragments of: α-synuclein (either wild type or any of the mutants associated to Parkinson's disease), huntingtin (as well as other proteins with expanded polyglutamine or polyalanine repeats), amyloid beta peptide (Aβ42), Prion protein, Islet amyloid polypeptide (hIAPP) or amylin, Superoxyde Dismutase, Tau, alpha-1-antitrypsin and other serpins, lysozyme, vitronectin, crystallins, Fibrinogen alpha chain, Apolipoprotein AI, Cystatin C, Gelsolin, Lactoferrin, Keratoepithelin, Calcitonin, Atrial natriuretic factor, Prolactin, Keratin, Medin (or full-length lactadherin), Immunoglobulin light chains, Transthyretin (TTR), apo-serum amyloid A protein (SAA), Beta2-microglobulin, Immunoglobulin heavy chains, or any other protein associated with any protein misfolding disorder.

The ability of a peptide sequence identified as described above to perform one or more the following may be determined:

i. stabilise a protein against aggregation;
ii. reduce the rate of loss of activity of a protein in storage;
iii. decrease the aggregation-mediated immunogenicity of a protein;
iv. increase the yields of proteins in in vitro translation systems;
v. increase the stability in solution of a formulation for therapeutic use;
vi. inhibit one or more cellular processes;
vii. prevent oligomerisation or multimerisation of a protein.

Further aspects of the present invention provide methods of designing aggregation inhibitors to treat protein misfolding diseases using the residue(s) identified in step d) of the above first aspect; designing compounds for stabilising proteins (e.g. biopharmaceuticals, antibodies, enzymes, etc.) against aggregations in formulations, vehicles and other solutions using the identified residue(s); designing compounds to increase the shelf life of such proteins using the identified residue(s); designing compounds to decrease immunogenicity of proteins due to aggregation using the identified residue(s); and designing compounds to increase the yields of proteins in in vitro translation systems using the identified residue(s).

Another aspect of the present invention provides a computer program which, when run on a computer, performs the method of any of the above aspects.

Another aspect of the present invention provides a computer data carrier containing a computer program according to the previous aspect.

A further aspect of the present invention provides a computer arranged to perform the method of any one of the above method aspects. Preferably this computer is a general purpose computer which is arranged to access databases containing information on known proteins for use in obtaining the prediction. Such databases may be stored locally, e.g. on a hard disk drive or in a memory, but are preferably stored remotely and accessed over a communications link such as a network or the internet.

BRIEF DESCRIPTION OF THE DRAWINGS

Embodiments of the invention will now be described with reference to the accompanying drawings, in which:

FIG. 1 shows the amyloid aggregation profiles of Aβ42 and α-syneuclein at pH 7;

FIGS. 5 and 5A show extracts from the pdb_seqres.txt and ss.txt files, respectively, obtained from the PDB;

FIG. 7 show an example output from the program for predicting hydrogen bonds between residues;

DETAILED DESCRIPTION OF THE PREFERRED EMBODIMENTS

Figure 2:
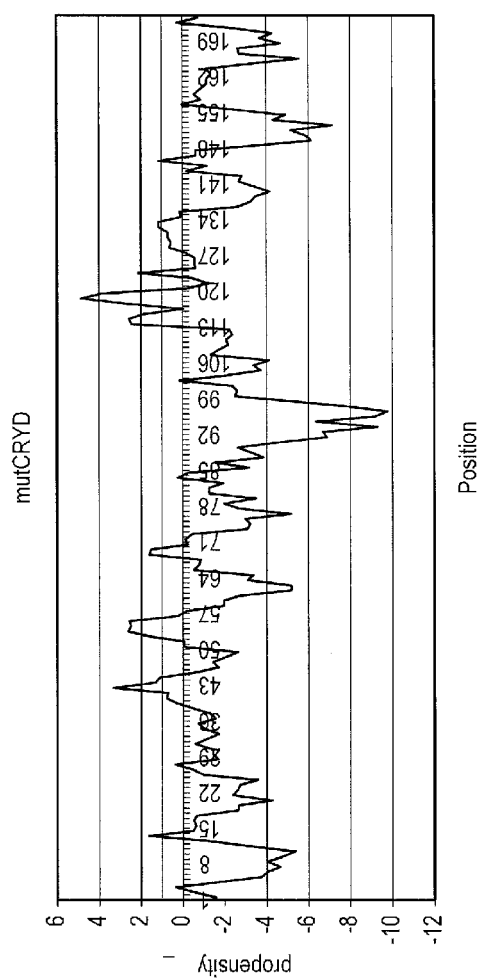
FIG. 2 shows the amyloid aggregation profile of a mutant of γ-crystallin D at pH 7.

Embodiments of the present invention will be described below. The methodology of the present embodiment will be demonstrated on a mutant of γ-crystallin D (mutCRYD). For the purposes of illustration, two further proteins are also discussed: α-synuclein, which is involved in Parkinson's disease, and Aβ42, which is associated with Alzheimer's disease.

mutCRYD is abundant in lens cells of the human eye. When misfolding, it can form aggregates that show up as cataracts leading to blurred vision or blindness (Héon E, Priston M, Schorderet D F, Billingsley G D, Girard P O, Lubsen N, Munier F L (1999) *The γ-Crystallins and Human Cataracts: A Puzzle Made Clearer*, Am. J. Hum. Genet. 65: 1261-1267, and Dahm R (2004) *Dying to see*, Sci. Am., 291(4): 52-59). γ-crystallin D and the mutant differ by three residues, R58H, R36S, and R14C, which were found to increase aggregation (Pande A, Pande J, Asherie N, Lomakin A, Ogun O, King J, Benedek G B (2001) Crystal cataracts: Human genetic cataract caused by protein crystallization, PNAS, 98(11): 6116-6120).

α-synuclein is a 140 residue protein which is found as a main component in Lewy bodies (dense deposits found in the brains of Parkinson's patients that may cause neurodegeneration—Spillantini M G, Schmidt M L, Lee V M Y, Trojanowski J Q, Jakes R, Goedert M (1997) *α-Synuclein in Lewy bodies*, Nature. 388: 839-840).

Aβ42 is a small hydrophobic peptide of 42 residues that might play a direct role in the interruption of synaptic function in Alzheimer's, the most common form of nerve pathology (Selkoe D J (2002) *Alzheimer's disease is a synaptic failure*, Science 298:789-790).

The propensity to form dense β-sheet-like structures, i.e. to aggregate, varies throughout a protein, depending on amino acid composition and sequence.

The aim of the method of the present embodiment was to identify candidate peptide sequences which would allow the speed and amount of aggregate formation to be reduced by blocking the aggregation-prone regions of the target proteins.

Identification of Aggregation Regions

So-called 'sensitive regions' for aggregation in parts of the two proteins α-synuclein and Aβ42 were predicted by Pawar A P, DuBay K F, Zurdo J, Chiti F, Vendruscolo M, Dobson C M (2005) *Prediction of "aggregation-prone" and "aggregation-susceptible" regions in proteins associated with neurodegenerative diseases*, J. Mol. Biol. 350: 379-392.

More generally, the above paper proposed an algorithm which allows the calculation of an aggregation propensity profile for a protein and which has been shown to give results which are in close agreement with a wide range of experimental measurements. For any given peptide sequence, it allows the calculation of propensity at every single residue or a propensity smoothed over a window of several amino acids. Table 1 lists the propensities at pH 7.0 for each amino acid separately.

TABLE 1

Aggregation propensities at pH 7.0 for each of the 20 naturally occurring amino acids separately.

| Residue | Propensity |
| --- | --- |
| Trp | 2.92 |
| Phe | 2.80 |
| Cys | 1.61 |
| Tyr | 1.03 |
| Ile | 0.93 |
| Val | 0.49 |
| Leu | −0.25 |
| Met | −1.06 |
| Thr | −2.12 |
| Ala | −3.31 |
| Gly | −3.96 |
| His | −4.31 |
| Ser | −5.08 |
| Gln | −6.00 |
| Asn | −6.02 |
| Asp | −9.42 |
| Lys | −9.55 |
| Glu | −10.38 |
| Arg | −11.93 |
| Pro | −11.96 |

FIG. 1 shows the aggregation propensity profiles for α-synuclein and Aβ42 calculated according to this algorithm (and presented in the above paper). The figure on the left shows the aggregation propensity profile of Aβ42 at pH 7. The aggregation profile for the unchanged wild-type Aβ42 sequence is plotted as the middle line, along with the maximum and minimum propensity values obtained after testing for any possible mutation at each amino acid position along the sequence. A line at $Z^{prof}_{agg}=1$ is drawn to aid in identifying aggregation-promoting regions. The same regions derived through experimental processes are shown as shaded regions.

Similarly, the figure on the right shows the amyloid aggregation profile of α-synuclein at pH 7, again including a line at $Z^{prof}_{agg}=1$ to aid in identifying aggregation-promoting regions. In this figure, the large region of protein thought to be structured in the fibrils is shown by the pale grey shading; the highly amyloidogenic NAC region is shown by the darker grey shading; and the 69-79 region, found to be a particularly amyloidogenic segment within that NAC region, is shown by the hashed lines.

Parts of a protein for which the score crosses a threshold (e.g. $Z^{prof}_{agg}=1$ in FIG. 1) are considered to have the highest propensity for aggregation and are assumed to be the core regions of aggregate and fibril formation in vivo. The predicted core aggregation regions from FIG. 1 are used in this embodiment as target sequences for the detection of any interaction partners that might act as inhibitors.

The methodology of the present embodiment will be demonstrated on mutCRYD.

FIG. 2 shows the aggregation propensity profile of mutCRYD, averaged over seven residues. As with the aggregation propensity profiles in FIG. 1, a line has been added at an aggregation propensity value of 1.0 to assist distinguishing between regions to be considered sensitive to aggregation, and other parts of the protein.

For further searching, residues 34 to 58 were selected. This region has two peaks predicting aggregation hotspots and contains two of the mutations. For a full analysis, all regions with an aggregation propensity larger than 1 would be considered, but the selected short fragment is sufficient to demonstrate the method used. The 24-residue query sequence is SARVDSGCWMLYEQPNYSGLQYFL (SEQ ID NO: 1) and will be referred to as mutCRYD34-58.

Searching—Overview

Although searching through a single file for a sequence is a standard procedure and can be carried out with most text editing programs or command line tools, there might easily be hundreds or thousands of hits in the file for short sequences. Considering each of them by hand, looking for secondary structure information, and then checking the PDB website for more information and using a 3D tool to visualize the structure and looking for inter-residue interactions in order to extract peptides that are closely linked via hydrogen bonds could take weeks or months for each protein.

Therefore proprietary software was developed to handle the process. The software was developed as a large number of small tools that were then step by step incorporated into a single, comprehensive program called PeptideSearch.

The programming language PERL was chosen for writing PeptideSearch, because all data used was available as plain text files and PERL offers powerful routines to parse through those files and extract and process information contained therein. PERL is also freely available software, prominent with bioinformaticians for these reasons.

Figure 4:
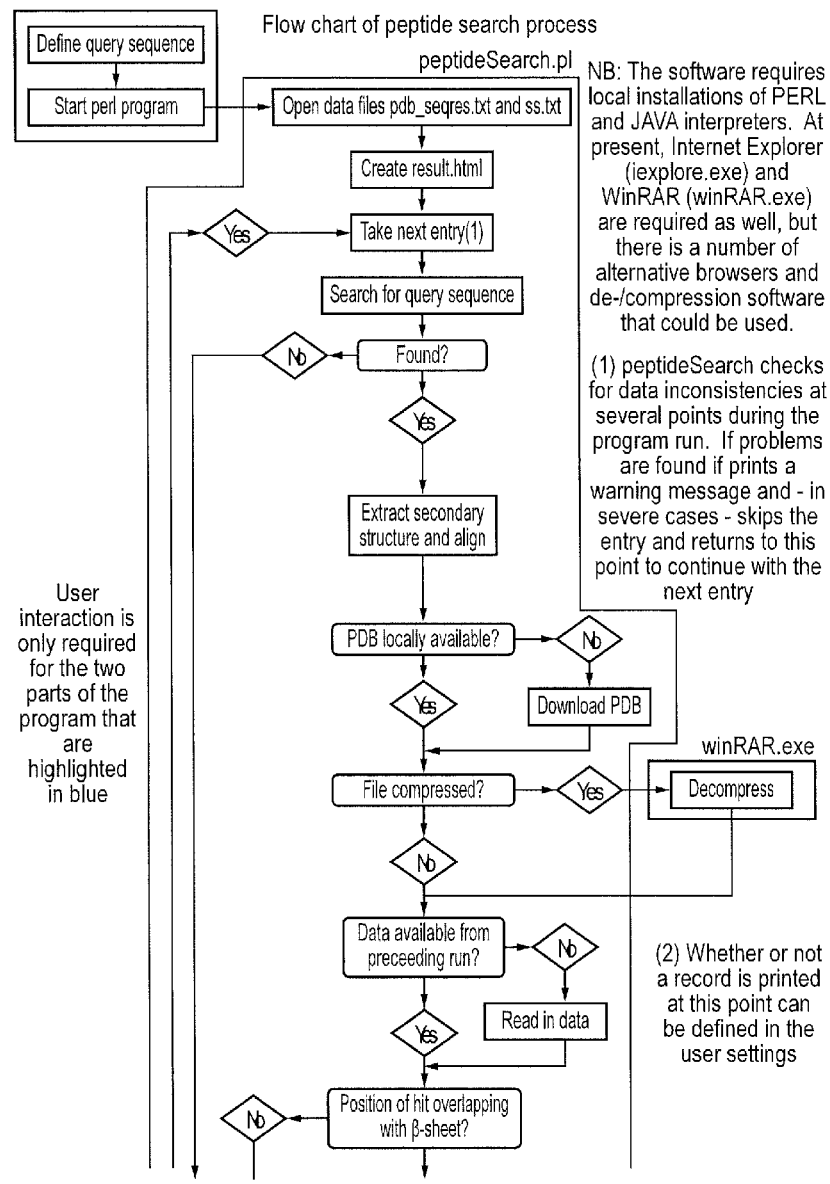
FIGS. 4 and 4A show a flow chart for the peptide search process.
Figure 4A:
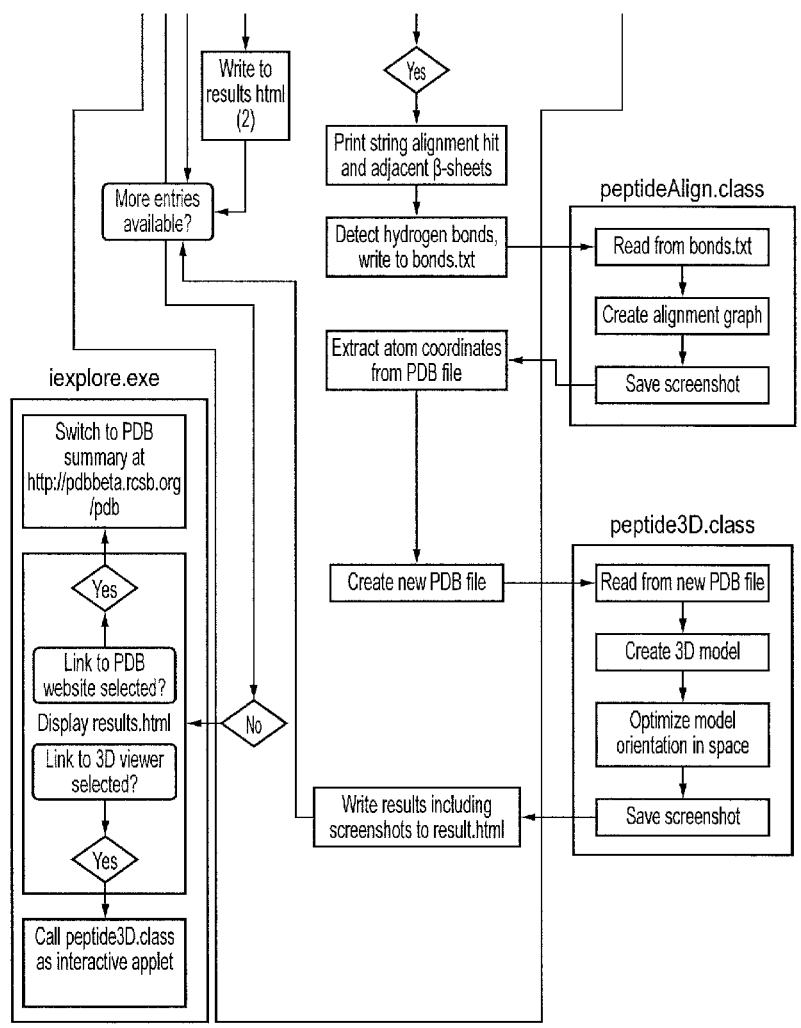

FIGS. 4 and 4A presents a flow chart of the software and the methodology of the present embodiment and provides an overview for the detailed explanation of the method which follows.

PeptideSearch relies on calls a number of external programs to extend its functionality. These calls are also shown in FIGS. 4 and 4A.

In using the program, the user input is the target sequence plus a number of parameters, and the program ultimately produces a concise summary of the candidate peptides including a three dimensional visualization of the peptides and their interaction partners. The time required to identify possible inhibitors for any protein was therefore reduced from potentially several weeks to a few hours.

Figure 3B:
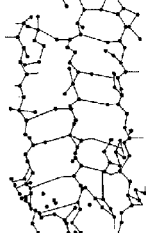
FIG. 3 shows the output of the PeptideSearch program for residues 1 to 8 of mutCRYD34-58.

PeptideSearch creates an HTML file called 'result.html' to keep records for each hit. This and all other files created by both the program and the external tools are stored in a new subdirectory. The name of this directory is derived from the current date and time so that the results of all program runs remain available on disk for later usage. While performing a search, PeptideSearch also prints information about hits to the command prompt or console, together with additional status messages. Once the program finishes its run, 'result.html' contains an overview over all hits that were found making it easy to select candidate peptides. The output of the program following a search for residues 1 to 8 of mutCRYD34-58 is presented in FIG. 3.

Searching

DETAILED DESCRIPTION

For the present embodiment, the search was based on the entries in the Protein Data Bank (PDB) of the Research Collaboratory for Structural Bioinformatics (RCSB) because this freely accessible online source contains a large number of experimental structures and theoretical models. Therefore, finding all or part of the query sequence within one of the peptide sequences in the PDB gives access to the related structure allowing identification of secondary structure and interaction partners.

The first stage of the search is to search for a target sequence in all of the protein entries in the PDB. This could have been achieved by mirroring the PDB files locally and parse each of them individually for the sequence of residues. However, this approach would be inefficient in terms of both time and space: as of Jun. 27, 2005, there were 31639 structures in the PDB, many of which as multimers with several chains.

The alternative, which was adopted for this embodiment was to take a single file containing all of the sequence information once and then to search through it in order to detect matches. Such a file is obtainable form the PDB ftp server of the RCSB at ftp://ftp.rcsb.org/pub/pdb/derived_data.

The file, pdb_seqres.txt, is a listing of all PDB sequences in FASTA format. Similarly, ss.txt, a file containing all secondary structures in the PDB in FASTA format can be found under the same address. The file versions used for this embodiment are dated Jun. 27, 2005.

The secondary structure file presents a first and fast source to perform sequence to secondary structure matching and to detect if a hit is involved in a β-sheet conformation.

FIGS. 5 and 5A show short excerpts from the two files: the first ten lines from seq_res.txt and ss.txt respectively. Table 2 below shows the meaning of the abbreviations used in ss.txt.

TABLE 2

| Abbreviation | Structure element | Abbreviation | Structure element |
|---|---|---|---|
| H | Helix | T | Hydrogen bonded turn |
| E | Extended beta strand | S | bend |
| G | 310 helix | B | Residue in isolated beta bridge |
| I | Pi helix | | |

Cleaning Sequence and Structure Files

The two files referred to above have been derived automatically by the PDB using data from all PDB entries. The secondary structure information in the PDB files has been determined by a number of different programs.

However, the two files are of unequal length. The extracts in FIGS. 5 and 5A show one of the reasons why: the FASTA header lines in the sequence file are longer containing more detailed information.

Considering the origin of the data one would expect that there should be one structure entry for every sequence and vice versa. Also, at first, it seems like the number of lines in the files might be identical making it very convenient to match the content of the two files.

However, neither of these assumptions are true: line numbers do not always match. A PERL script running through the file extracting all FASTA header lines returned 74560 entries for pdb_seqres.txt and 69903 entries for ss.txt. There are a number of other problems that needed to be solved before the files could be used as input. For example, usage of IDs was not consistent within and between the two files. The sequence file uses IDs such as 1tsv_, and distinguishes different chains as 1thl_, 1thl_1, 1thl_2, or as 1pr2_A, 1pr2_B, while ss.txt uses 1TSV:_, 1THL:_, 1THL:_:1, 1PR2:A, 1PR2:B, instead. Also, there are many IDs in the sequence file that do not have a corresponding entry in the secondary structure file, and vice versa: entries such as 1J3W, 1OG8, and 1VGS are contained in ss.txt but not in pdb-seqres.txt. They have been replaced by IDs 2CVZ, 2BUH, and 2CV4 in the Protein Data Bank, which is only accounted for in pdb_seqres.txt.

It took a number of PERL scripts to remove all unique entries from both files. The resulting files then contained 68383 matching entries.

A potential problem still remains in that some of the sequences do not match in length. The PeptideSearch program was arranged to point out such inconsistencies during run time.

Matching Query to Sequences

Experimental structures of interest are those in which the amino acid sequence from the query string occurs. This means that one needs to search for the exact matches of the forward string, for mutCRYD34-58:

SARVDSGCWMLYEQPNYSGLQYFL as well as for the inverted sequence, here:

LFYQLGSYNPQEYLMWCGSDVRAS.

It is clearly far less likely to find an exact sequence match in the PDB for long peptides than it is for short ones. Indeed, when searching for matches for a complete protein, it is very likely that only one match will be found: the protein itself.

Even when concentrating on the sensitive region of a protein, one might want to search for hits with stretches of amino acids that are simply too long to give exact hits in the PDB. Since the structure of the mutant of γ-crystallin D is not included in the PDB there is no result for the full 24-residue sequence.

To increase the yield of hits, two further methods were implemented.

First, the target protein sequence was divided into substrings interaction partners were searched for each of these substrings. This allows peptides that bind to part of the sequence to be identified. These can later be tested separately, for example in combination with other peptides, or be engineered into a longer peptide by joining several such peptides together.

In the PeptideSearch program, the user can set a minimal length n and a maximal length m of the search sequence. Following trials, a length of query sequence in the range 5 to 8 residues was found to give a sufficient number of hits while finding interaction partners that were still long enough to still be useful. However, other length substrings may also be used.

The program is arranged to automatically runs a full search for all contiguous substrings of the initial sequence with a length in the given range. The total number of query sequences q searched for a full query sequence of length l is therefore:

$$q = \frac{(l-n+1)\cdot(l-n+2)-(l-m)\cdot(l-m+1)}{2}$$

Second, the program allows the use of regular expressions. This allows variability to be introduced into the search sequence. Accordingly, PeptideSearch allows conservative substitutions to be defined that are taken into account when searching through the amino acid sequence file.

For example, according to Table 1, Gln (Q) and Asn (N) have similar aggregation propensities and therefore one option to increase the number of useful hits would be to consider both in a search. The regular expression of a search string, e.g. QANT (SEQ ID NO: 3) would then be [QN]A[QN]T (SEQ ID NO: 3-6). Other substitutions based on the aggregation properties of the residues can be used in a similar fashion.

The two methods can be combined, so that each possible sub string down to a minimal length is converted into a regular expression which considers the conservative substitutions described above.

Finding Secondary Structure Elements

Data from both pdb_seqres.txt and ss.txt is read once at the start of the program and stored in large arrays. Entries from both arrays are then processed jointly. Since, as noted above, the length of amino acid sequence and structure do not always match, the line numbers cannot be used as lead. Instead the FASTA header lines serve as guide in order to make sure that the search considers entries that belong together and that the information in both files remains synchronized.

If entries are split over several lines, they are concatenated by removing the line breaks between them. This creates two string variables for each entry, one for the complete amino acid sequence and one for the respective secondary structure. If, at this point, the two strings are of unequal length, then the information given is no longer considered as being reliable. In this case, the program displays a warning to make the user aware of the inconsistency and suggests a manual inspection of the hit.

PERL provides a simple to use routine for searching the sequence string for occurrences of the query sequence, either looking for perfect matches, or by matching regular expressions. If there are any hits then PeptideSearch extracts them from the sequence string and aligns them with the corresponding region of the secondary structure string. This allows a first visual check of how many of the residues in the match are in an extended β-sheet formation.

Since the neighbourhood of a structure might be of interest as well, the program is also arranged to output a number of residues and structure information both to the left and to the right of the match. The size of this window can be set in the program options.

Ideally, this information could simply be used to select all those entries for which the secondary structure file indicates the presence of β-sheets and subsequently only investigate those further. However, with the files used, this would result in many false positives as well as many false negatives. The main reason for this is that the prediction in ss.txt is frequently inaccurate. This has been found when comparing the alignment with the actual structure in the PDB file.

Therefore, it turned out to be better to consider every hit in a sequence regardless of the information in ss.txt. This increases the number of hits that have to be processed further requiring accessing the PDB, but it also ensures that no important candidate peptide is missed.

Retrieving PDB Files

Once the query sequence has been detected in one of the entries, more information needs to be obtained and it is necessary to process the actual PDB file. The PDB ID is being extracted from the FASTA header line. A local PDB directory is defined in PeptideSearch.

If the PDB file that belongs to this ID is available in the local directory, be it compressed or uncompressed, then this local copy is used. Otherwise PeptideSearch uses one of its routines to automatically access the mirror of the RCSB Protein Data Bank ftp server at the Cambridge Crystallographic Data Centre (CCBC), ftp://pdb.ccdc.cam.ac.uk/rcsb/data/structures/divided/pdb/, and downloads a compressed copy of the PDB file. This .Z-archive is then extracted via a system call to the program WinRAR.

Processing PDB Files

Before opening a PDB file the program checks whether the same PDB ID was used for the preceding hit. This might be the case if there are several hits within the same amino acid sequence, or when the structure in a file is a multimer so that there are analogous hits on each chain. If the ID is the same then the data is still contained within the program's data arrays and can be reused, saving a significant amount of time. Otherwise, the local copy of the PDB file is opened and the data is read to memory.

There are two parts of each file that are of interest. The first are the lines that can be used to identify overlap of the query sequence with β-sheets. These begin with the "SHEET"-tag that show the positions of β-sheets.

The second refers to the "ATOM" entries that give the coordinates for each particle in a molecule. This information allows for the prediction of hydrogen bonds, since knowing which residues actually interact provides important information and gives the researcher more freedom in designing inhibitor peptides. For example, residues whose side chains are not involved in the interaction, might be replaced by others, that provide the peptide with better biochemical properties.

For every strand in a β-sheet there is one "SHEET" line. This contains the index of the first and last residue in the strand. If this strand is not the first in the sheet then the line also contains the two residues where this and the previous strand have been registered, i.e. indices of a single pair of residues found to be connected by a hydrogen bond. Full information about "SHEET" and "ATOM" entries can be found at http://www.rcsb.org/pdb/docs/format/pdbguide2.2/guide2.2_frame.html.

Extracting the information from those lines and the start and end points of the hit in the amino acid sequence provides a test for overlap: if the start index of the sheet is not larger than the index at the end of the hit and the end index of the sheet is not smaller than the start of the hit then there is overlap, in which case the number of overlapping residues is calculated.

Ideally the number of overlapping residues should not be too small because it defines the length of the potential inhibitor peptide. An inhibitor that consists of only a few residues might not be very efficient, and it will be hard to design a stable peptide with favourable properties. The program enables the user to define a threshold and excludes all hits with overlaps shorter than this threshold from output into 'result.html'.

The β-strand which overlaps with the query sequence and the adjacent strands (either one or two, depending on the position of the first strand in the sheet), are then displayed in an alignment that takes into account strand orientation (parallel or anti-parallel) and registration.

For example, if the peptide sequence is 'ADDYYTATGH-WYAT" (SEQ ID NO: 7) and the strands run from residues 1 to 4, 6 to 10, and 12 to 14, respectively, in anti-parallel β-sheet formation with registration at 3 and 7, and 9 and 13, then the alignment results in:

ADDY (SEQ ID NO: 8)
HGTAT (SEQ ID NO: 9)
YAT

In 'result.html' the residues of the query sequence in this alignment would then be shown in red. If the search was looking, say, for occurrences of 'ATGHW' (SEQ ID NO: 10), which would have been found at indices 7 to 11 in the peptide sequence above, then the residues 'HGTA' (SEQ ID NO: 11) would be highlighted in the alignment.

The alignment allows rapid screening of hits for those with a large overlap between query sequence and β-sheet. It shows how many and which of the residues form a β-sheet, and consequently how many and which of the residues can be blocked if their interaction partners were to be incorporated into short inhibitor peptides.

Although the above searching methodology provides one route to the identification of candidate peptides, it is not foolproof on the current data available. In particular, the indices of residues found in 'SHEET' lines refer to indices in 'ATOM' lines, but not to the 'SEQRES' records in the same file. The Protein Data Bank assures that references to 'ATOM' records are tested for correctness. The data in 'pdb_seqres.txt', however, was derived from the 'SEQRES' records, and their indices are often not the same. For example, a 'SEQRES' entry might start with MET, while the first 'ATOM' entry is a SER, or the sequences may be the same, but the first 'ATOM' entry starts with residue index 21, and not 1.

This means that, although the above technique showing alignment might reproduce the relative β-sheet strand positions correctly, the identifier of the residues might be taken from the wrong part of the amino acid sequence. This also means that the identification of an overlap with a β-sheet might have been incorrect in the first place: the query sequence could actually be located at a different position in the structure.

peptideAlign.class

To make sure that such an event can be detected when looking at the summary of this hit later, a further alignment method was developed using the 'ATOM' entries. This allowed an alternative method for deriving candidate peptides, or for a cross-check on the results obtained from the 'SHEET' searching described above.

This alignment method also includes detecting and displaying hydrogen bonds between residues, rendering the alignment much more informative.

The following algorithm was devised for searching in the 'ATOM' data: for all pairs of atoms that are at least three residues apart and are within the interesting part of a β-sheet, calculate the Euclidean distance between them (using the standard formula $d=\sqrt{\Delta x^2+\Delta y^2+\Delta z^2}$, where d is the Euclidean distance, and $\Delta x$, $\Delta y$, and $\Delta z$ are differences in the respective coordinates).

If the calculated distance is less than 3.075 Angstrom then the indices of this pair of residues are pushed onto a hydrogen bond storage array. The cut-off length was chosen from literature and is large enough to detect most hydrogen bonds between backbone atoms and side chains while it is small enough to keep the number of false positives low.

After completing the prediction, strand and bond information is written to a file called 'bonds.txt'. This file is used as intermediate data storage to share information with another application: 'peptideAlign.class', a Java-based tool that was created for drawing a graphical β-sheet alignment. Although PERL has powerful routines to process large amounts of text, Java offers easier to use graphical functions. Therefore the properties of both programming languages were combined by having 'peptideSearch.pl' use a system call to link out to PeptideAlign. The latter creates a screenshot of an alignment which the PERL program then includes into the overview of the current hit in 'result.html'.

Figure 6:
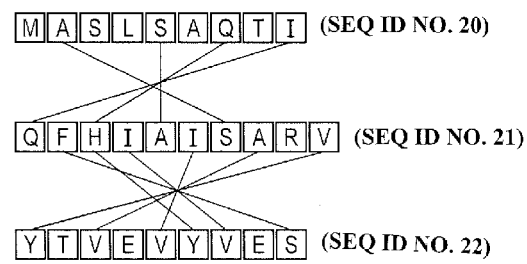
FIG. 6 shows the prediction of hydrogen bonds in three adjacent strand in a β-sheet.
Figure 8:
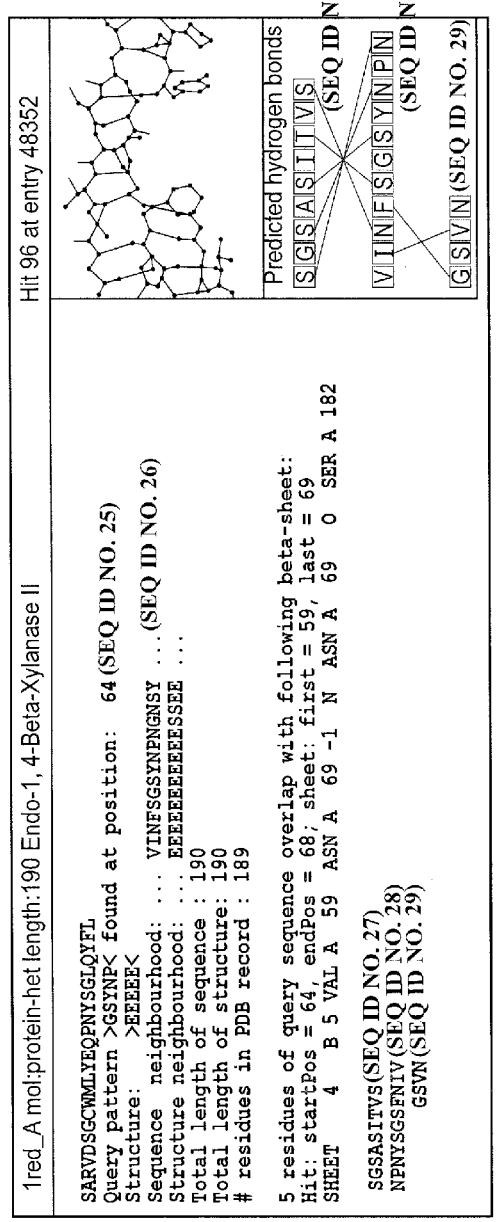
FIG. 8 shows a result summary for a hit in the peptide searching.
Figure 9:
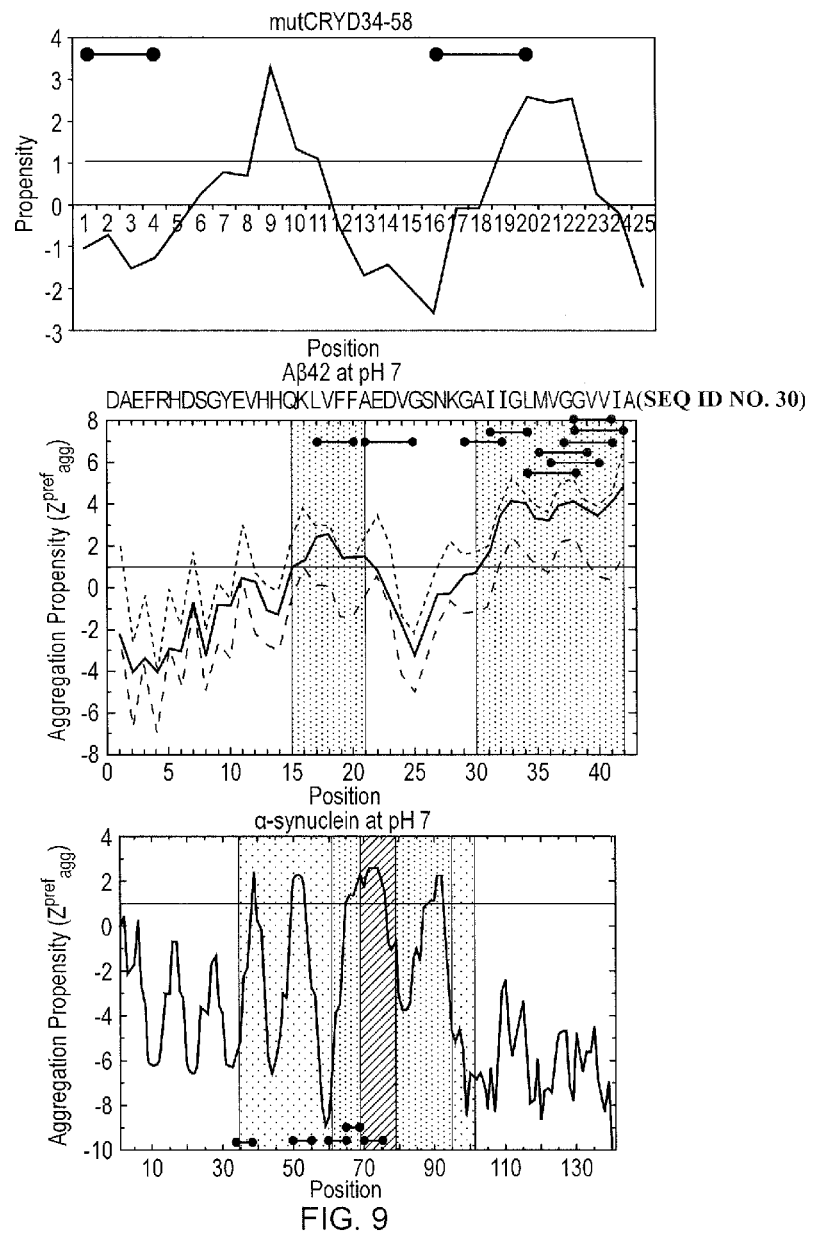
FIG. 9 shows aggregation propensity profiles for mutCRYD34-58, Aβ42 and α-synuclein with indications of the positions at which short peptide matches were found in the PDB.

Using graphics facilitates the indication of hydrogen bonds between residues, which can be done by simply drawing lines. PeptideAlign does not directly account for anti-parallel β-sheet formation, but the graphical output does indicate if a strand's orientation should be inverted as in this case the hydrogen bonds cross each other. For example, the blue lines indicating hydrogen bonds in FIG. 6 show that orientation of the middle strand needs to be inverted. A further algorithm is used to correctly orientate the strands and shift them relative to each other in order to minimize the total length of bonds.

PeptideAlign reads peptide and bond information from 'bonds.txt', along with a name for the anticipated output image file. Image file names are of the form hitX.png where X indicates the consecutive number of the hit. The program translates the information in the file into a graphical representation and returns control to peptideSearch. An example output is shown in FIG. 7: the file contains path and name of the file to which the screenshot is supposed to be saved, the numbers of atoms and bonds in the file followed by the residue IDs for all atoms and information about which of them are linked by bonds; the graphical representation on the right shows which residues are linked to each other.

Minimalist PDB File

The alignment generated by the 'ATOM' searching is accurate thanks to the curation at the PDB. If this corresponds to the one created by PeptideSearch then the 'SEQRES' record is consistent as well. Otherwise, the user will need to check the graphical overview visually for an overlap. If there is none, a manual check of the PDB file is required to see if there is a different β-sheet that contains part or all of the query sequence.

Note that, at present, it is not possible to create the amino acid sequence anew from the 'ATOM' record and to search this for the occurrence of the query string. This is because residues are often missing from the record. For example, in pdb1p9w.ent residue 108 is followed by residue 121. The gaps can be explained in a number of ways, for example by insufficient experimental data, low NMR or X-Ray resolution, or highly flexible side chains that result in blurred signals making an exact determination of atom positions impossible. Another explanation is simply that the research providing the data is sometimes only interested in a particular part of a protein, e.g. an active site, and therefore does not provide any prediction of the remaining structure. However, where more complete data is available, such a searching method would be an appropriate stand-alone alternative to the 'SHEET' searching discussed above.

Having found a hit in a β-sheet, it is then possible to see which of the residues interact and build a scaffold for designing candidate peptides. For example, residues that do not interact with the residues in the query sequence might be replaced by other amino acids, allowing a larger range of peptides to be designed and tested.

For example, in the short alignment in FIG. 6, SARV (SEQ ID NO: 12) interacts with VTY. Hydrogen bonds are predicted between A and V, and V and Y. However, T does not seem to interact with the query sequence at all, so the peptide VXY, could be used as a scaffold for creating candidate peptides, with X being replaceable by different amino acids. Realistically such a scaffold is most likely too short to be effective, hence the preferred searching for peptides with lengths of 5 residues and more.

For each successful hit PeptideSearch creates a new .pdb file containing the coordinates of all atoms involved in the β-sheet. To do this it extracts that part of the complete structure that contains the β-strands with the query sequence fragment and its interaction partners.

The file can be opened with any of the usual 3D viewers such as Rasmol or vmd and permits to efficiently verify predicted hydrogen bonds and spatial orientation of side chains.

Peptide3D.class

To give a preview of the structure in the new .pdb file screenshots are included into the records in 'results.html'. To do so a 3D viewer was required that would allow rendering the molecules, placing them into an informative orientation in space, and taking a screenshot, all without requiring user interaction.

Results.html

Once PeptideSearch has finished running all possible substrings and mutations through all entries in pdb_seqres.txt, it opens a browser window with a system call and presents all the hits it has found in an overview. This overview offers links to the PDB summary page for the PDB ID related to each hit and a link to Peptide3D which is implemented as an applet allowing to view the structure in an 800×600 pixel format.

Results

Running the software with mutCRYD34-58 as input, setting the minimal and maximal substring length to five, allowing no mutations and excluding all hits in which the overlap with a β-sheet is smaller than four resulted in 153 exact matches in pdb_seqres.txt, 47 of which were in β-sheets.

Only eight of these results were longer than three residues and the latter were included in 'result.txt'. In fact, this set actually only gives two distinct hits, because the first two and the last six matches are practically identical since they are from the different chains of a multimer.

The first of those hits refers to the sequence SARVD (mutCRYD34-58 residues 1 to 5; SEQ ID NO: 13) that was found in the Putatinve Glycine Cleavage System Transcriptional Repressor (PDB ID 1U8S). This is the hit for which the result is presented in FIG. 3. The four-residue overlap is depicted in FIG. 6.

The second hit was found for the sequence PNYSG (mutCRYD34-58 residues 15 to 20; SEQ ID NO: 14) in Endo-1, 4-Beta-Xylanase II. The result summary for this hit from the HTML file is shown in FIG. 8.

FIG. 9 highlights the two hits in the aggregation propensity profile of mutCRYD34-58. The locations of exact matches near or close to the aggregation hotspots of the two proteins α-synuclein and Aβ42 are also shown in the respective profiles in FIG. 9. For α-synuclein, the length of sub-strings was set to the range 6 to 7, and for Aβ42 it was set to 5.

For mutCRYD, the first hit might not be very effective as a candidate for an aggregation inhibitor as it does not lie within the sensitive region for aggregation. The second hit however, has the potential to block the peptide from initiating formation of aggregates at this site.

For the other two proteins, each of the interaction partners corresponding to the hits shown has the potential to act as aggregation inhibitor. The number of hits for α-synuclein increases strongly when the sub-string length is set to 5.

The results of the analysis of α-synuclein are the subject of a further patent application by the present applicant.

A series of peptides were designed to interact with regions 61-66 (EQVTN (SEQ ID NO: 15)) and 71-76 (VTGVT(SEQ ID NO: 16)) of α-synuclein using the software described above.

This analysis identified a peptide consisting of a sequence of D-amino acids which interacts with a region of α-synuclein between residues 61-66 (EQVTN (SEQ ID NO: 15)). One suitable peptide comprises or consists of the D-amino acid sequence QYSVLI (ZP-0195 described in Table 3 below). Other suitable peptides may comprise or consist of the D-amino acid sequence QYSVLI with one, two or three amino acid substitutions. For example, a peptide may consist of a D-amino acid sequence selected from the group consisting of: qykvli, qysvpi, qyspli, qypvli, rysvli, qysvli, qytvli, pysvli, or qysvlv.

The peptide may comprise one, two or three additional N terminal residues.

For example, a peptide may comprise or consist of a sequence selected from the group consisting of: ekysvli and drysvli.

The analysis also identified a peptide consisting of a sequence of D-amino acids which interacts with a region of α-synuclein between residues 71-76 (VTGVT (SEQ ID NO: 16)). For example, a peptide may consist of the D-amino acid sequence of hhviva (ZP-0158) or may comprise or consist of the D-amino acid sequence hhviva with one, two or three amino acid substitutions. Preferably, the N-terminal histidine residues are not substituted.

For example, a peptide may comprise or consist of a sequence selected from the group consisting of: hhvvva, hhvlva, hhvkva, hhveva, hhviva, hhvivp, hhvivv, hhvivt, hhvivy, hhvivw, hhtivv, hhtivk, hhtvva, hhtiva, hhtivv, hhtevy and hhttvy.

For the region 61-65, the peptide Ac-qysvli-NH2 (ZP-0195) was designed to interact and prevent aggregation. Variations of this sequence were also tested where one or more of the amino acids at any give position was substituted with another and variations were made at the N-terminus such as the addition of an extra amino acid and acetylation (ZP-0195 to ZP-0230).

For the region 71-75 the peptide Ac-hhviva-NH2 (ZP-0158) was designed to interact and prevent aggregation.

Variations of this sequence were also tested where one or more of the amino acids at any give position was substituted with another. All peptides tested were N-terminal acetylated and the 2 histidines at the beginning of the sequence were kept constant in all designs (ZP-0158 to ZP-0194).

All peptides were tested for inhibition of ASYN aggregation in TBS by carrying out aggregation assays with 50 μM ASYN and 100 μM inhibitor with 50 mM tris and 150 mM NaCl and 20 μM Thioflavin T. The reaction volume was 200 μL. Each reaction was set up in a 96 well polypropylene plate with ASYN only and buffer only controls. The reactions were incubated at 37 C with shaking for 48 hours and aggregation was monitored by reading thioflavin T fluorescence.

The kinetic traces were fitted using Zyentiafit software which fits the data to a Sigmoidal function $f(x)=k+A/(1+\exp(-b(t-t0)))$ from which the lag time, rate of aggregation and total change in ThT fluorescence may be calculated.

Peptides were ranked according to their effectiveness and table 3 below shows those sequences chosen for further study. The choice was based on the peptide having more than a 20% increase in lag time and/or more than 20% decrease in ThT fluorescence or aggregation rate.

TABLE 3

Peptide sequences designed to interact with regions 61-66 and 71-76 of ASYN which show effectiveness at preventing ASYN aggregation in-vitro.

| Zyentia Code | Sequence | % decrease in ThT fluorescence | % decrease in rate of aggregation | % increase in Lag phase |
|---|---|---|---|---|
| ZP-0158 | Ac-hhviva-NH2 | 15.1 | 18.4 | 32.5 |
| ZP-0159 | Ac-hhvvva-NH2 | 19.8 | 18.6 | 36.6 |
| ZP-0160 | Ac-hhvlva-NH2 | 8.8 | 10.5 | 36.5 |
| ZP-0161 | Ac-hhvkva-NH2 | −5.9 | 2.3 | 19.7 |
| ZP-0162 | Ac-hhveva-NH2 | 6.3 | 6.6 | 33.4 |
| ZP-0164 | Ac-hpviva-NH2 | 3.7 | −2.3 | 43.0 |
| ZP-0168 | Ac-hhvivp-NH2 | −8.6 | −5.4 | 29.8 |
| ZP-0169 | Ac-hhvivv-NH2 | −0.5 | −13.3 | 26.1 |
| ZP-0170 | Ac-hhvivt-NH2 | 24.5 | 29.3 | 29.4 |
| ZP-0171 | Ac-hhvivy-NH2 | 13.9 | 13.2 | 43.6 |
| ZP-0172 | Ac-hhvivw-NH2 | −1.7 | 6.9 | 28.1 |
| ZP-0175 | Ac-hhtivv-NH2 | 21.9 | 16.8 | 89.7 |
| ZP-0179 | Ac-hhtivk-NH2 | 0.6 | −0.6 | 30.4 |
| ZP-0180 | Ac-hhtvva-NH2 | 19.8 | 18.4 | 30.3 |

TABLE 3-continued

Peptide sequences designed to interact with regions 61-66 and 71-76 of ASYN which show effectiveness at preventing ASYN aggregation in-vitro.

| Zyentia Code | Sequence | % decrease in ThT fluorescence | % decrease in rate of aggregation | % increase in Lag phase |
|---|---|---|---|---|
| ZP-0181 | Ac-hhtlva-NH2 | 22.8 | −1.2 | 29.4 |
| ZP-0186 | Ac-hhtlvv-NH2 | 30.7 | 29.7 | 16.1 |
| ZP-0193 | Ac-hhtevy-NH2 | 8.7 | −15.8 | 31.4 |
| ZP-0194 | Ac-hhttvy-NH2 | 11.6 | 7.7 | 38.8 |
| ZP-0202 | Ac-qykvli-NH2 | 53.5 | 54.5 | −28.8 |
| ZP-0204 | Ac-qysvpi-NH2 | 1.4 | −5.6 | 23.6 |
| ZP-0205 | Ac-qyspli-NH2 | 16.6 | −11.9 | 30.6 |
| ZP-0206 | Ac-qypvli-NH2 | 3.3 | 8.4 | 25.9 |
| ZP-0207 | Ac-qpsvli-NH2 | 5.5 | 3.6 | 29.7 |
| ZP-0212 | Ac-rysvli-NH2 | 51.1 | 44.9 | −14.4 |
| ZP-0213 | Ac-ekysvli-NH2 | 25.6 | 12.9 | 29.4 |
| ZP-0214 | Ac-drysvli-NH2 | 20.4 | 4.8 | −12.6 |
| ZP-0215 | NH3-qysvli-NH2 | 27.6 | 17.5 | 3.1 |
| ZP-0221 | NH3-qytvli-NH2 | 24.7 | 22.8 | −22.4 |
| ZP-0222 | NH3-qykvli-NH2 | 42.3 | 34.3 | 7.7 |
| ZP-0228 | NH3-pysvli-NH2 | 40.8 | 46.2 | 38.2 |
| ZP-0229 | NH3-qysvlv-NH2 | 17.8 | 24.3 | 33.5 |

Design of Compounds from the Results

Hits identified by the methods or software tools described above may be used as templates to design aggregation inhibitors or stablisers. Molecular dynamic or other suitable computation methods can be used to test libraries of compounds based on these templates for their affinity to the target sequence.

Computational methods may make use of specific force-fields and energy minimisation routines to a variety of inhibitors based on the template, in order to maximise the interaction between inhibitor and target aggregating polypeptide. (see Das B, Meirovitch H, Navon I M, *Performance of hybrid methods for large-scale unconstrained optimization as applied to models of proteins*, J Comput. Chem. 2003; 24:1222-31 and de Bakker P I, DePristo M A, Burke D F, Blundell T L, *Ab initio construction of polypeptide fragments: Accuracy of loop decoy discrimination by an all-atom statistical potential and the AMBER force field with the Generalized Born solvation model*, Proteins, 2003; 51(1):21-40).

Selected compound libraries may be tested in vitro in aggregation assays to identify lead compounds that would inhibit the aggregation of the target polypeptides.

Retro-enantio derivatives (reversed C—N sequence and D-amino acids) may be used when the stabiliser/aggregation inhibitor needs to be resistant to other proteases.

The identified stabiliser/aggregation inhibitor may be fused to other proteins/peptides. A protein/peptide fused to a stabiliser/aggregation inhibitor may: act as carriers in order to target delivery to specific areas of the body, specific organs, specific cell types, etc.; facilitate intra-cellular delivery; facilitate blood-brain-barrier translocation; increase the half-life in plasma; and/or interact with another protein or receptor.

The invention claimed is:

1. A method for predicting potential protein aggregation inhibiting peptide sequences, including the steps of:
   a) identifying a peptide sequence forming at least part of an aggregation region in a target protein;
   b) testing, using a processor, in a plurality of protein structures, whether said peptide sequence forms part of a β-sheet, in which the step of testing is carried out on a plurality of heterologous proteins to said target protein;
   c) if a positive result is achieved in step b), extracting information corresponding to the adjacent strands of that sheet;
   d) identifying a plurality of contiguous residues in the strands adjacent to said peptide sequence whose side chains interact with said peptide sequence, those residues forming a potential protein aggregation inhibiting peptide sequence.

2. A method according to claim 1 wherein the step of testing is carried out using a database of protein structures.

3. A method according to claim 2 wherein the step of testing includes the sub-steps of: identifying a group of proteins contained in said database which contain related peptide sequences related to said peptide sequence; and identifying within said group those proteins in which said related peptide sequences form part of a β-sheet.

4. A method according to claim 3 wherein said related peptide sequences include said peptide sequence in both forward and reverse order.

5. A method according to claim 3 wherein said related peptide sequences include said peptide sequence and fragments of said peptide sequence.

6. A method according to claim 3 wherein said related peptide sequences include sequences containing conservative substitutions of one or more amino acids within said peptide sequence.

7. A method according to claim 6 wherein said conservative substitutions are chosen on the basis of amino acids with aggregation propensities at pH 7.0 of within 0.2 of each other.

8. A method according to claim 3 wherein the sub-step of identifying includes comparing said related peptide sequences with the residues contained in "SHEET" lines in a PDB file for the protein in question.

9. A method according to claim 3 wherein the sub-step of identifying includes identifying those residues in said related peptide sequences that form hydrogen bonds with each other.

10. A method according to claim 9 wherein, in order to identify those residues that form hydrogen bonds with each other, the Euclidean distance between each pair of residues which are at least three residues apart is calculated, and a hydrogen bond is assumed to form if that distance is less than 3.075 Angstrom.

11. A method according to claim 10 wherein the Euclidian distances are calculated using "ATOM" entries from the PDB file for the protein in question.

12. A method according to claim 10 further including the step of displaying the identified residue pairs that form hydrogen bonds and the hydrogen bonds between them.

13. A method according to claim 8 wherein the results obtained are compared to results obtained by carrying out a method according to claim 11 to cross-check the identified residues.

14. A method according to claim 1 wherein the residues identified in step d) are those residues whose side chains interact with said peptide sequence via hydrogen bonds.

15. A method according to claim 1 wherein the step a) of identification uses an aggregation propensity profile.

16. A method according to claim 15 in which the step a) of identification selects peptide residues with an aggregation propensity greater than 1 in said aggregation propensity profile.

17. A method according to claim 1 wherein the step a) of identification is performed experimentally.

18. A method according to claim 1 further including the step of displaying the residues identified in step d).

19. A method according to claim 18 wherein the step of displaying includes displaying the 3-dimensional arrangement of the identified residues in the β-sheet.

20. A method according to claim 1 further comprising the step of:
 testing whether the residues identified in step d) interact with one or more other proteins.

21. A method according to claim 20 in which the step of testing is carried out on a plurality of heterologous proteins to said target protein.

22. A method according to claim 21 wherein the step of testing is carried out using a database of protein structures.

23. A method according to claim 22 wherein said protein structures are structures which mediate essential cellular processes.

24. A method according to claim 22 wherein the step of testing includes the sub-steps of: identifying a group of proteins contained in said database which contain related peptide sequences related to said peptide sequence; and identifying within said group those proteins in which said related peptide sequences interact with said identified residues.

25. A method according to claim 1 wherein the part of the aggregation region identified in step a) is part of a helix, a loop, beta-turn or beta-bulge.

26. A method according to claim 1 comprising producing a protein aggregation inhibiting peptide comprising the residues identified in step d).

27. A method according to claim 1 further comprising the steps of:
 e) synthesising a peptide library, the members of said peptide library comprising the residues identified in step d), and
 f) determining the affinity of the members of said library for the target protein.

\* \* \* \* \*